US010105317B2

(12) United States Patent
Yu et al.

(10) Patent No.: US 10,105,317 B2
(45) Date of Patent: Oct. 23, 2018

(54) METHOD OF DRUG DELIVERY

(75) Inventors: Chris C. Yu, Conneautville, PA (US); He Yu, Cheshire, CT (US)

(73) Assignee: Anpac Bio-Medical Science Co., Ltd., Tortola (VG)

( * ) Notice: Subject to any disclaimer, the term of this patent is extended or adjusted under 35 U.S.C. 154(b) by 1300 days.

(21) Appl. No.: 12/498,698

(22) Filed: Jul. 7, 2009

(65) Prior Publication Data

US 2011/0008446 A1 Jan. 13, 2011

(51) Int. Cl.
*A61K 9/00* (2006.01)
(52) U.S. Cl.
CPC .................................. *A61K 9/0097* (2013.01)
(58) Field of Classification Search
None
See application file for complete search history.

(56) References Cited

U.S. PATENT DOCUMENTS

| | | | |
|---|---|---|---|
| 6,165,440 A | | 12/2000 | Esenaliev |
| 6,663,615 B1 * | | 12/2003 | Madou et al. ............. 604/891.1 |
| 7,182,894 B2 | | 2/2007 | Kumar et al. |
| 2002/0034474 A1 | | 3/2002 | Sabel et al. |
| 2002/0068187 A1 | | 6/2002 | O'Connor et al. |
| 2003/0007991 A1 | | 1/2003 | Masters |
| 2004/0096477 A1 | | 5/2004 | Chauhan et al. |
| 2004/0236278 A1 | | 11/2004 | Herweck et al. |
| 2006/0040390 A1 | | 2/2006 | Minor, Jr. et al. |
| 2006/0283465 A1 | | 12/2006 | Nickel et al. |
| 2007/0243401 A1 | | 10/2007 | Hirata et al. |
| 2008/0241264 A1 * | | 10/2008 | Solomon ....................... 424/490 |
| 2008/0243303 A1 | | 10/2008 | Solomon |
| 2008/0279764 A1 | | 11/2008 | Manganaro et al. |
| 2009/0028910 A1 | | 1/2009 | Desimone et al. |
| 2009/0081461 A1 | | 3/2009 | Yi et al. |
| 2009/0131738 A1 | | 5/2009 | Ferren et al. |

FOREIGN PATENT DOCUMENTS

| WO | WO 2004/101023 | * 11/2004 |
|---|---|---|
| WO | 2009018467 | 2/2009 |

OTHER PUBLICATIONS

Binggeli et al. (Cancer Research, 1830-1835, 1980) Cellular Potentials of Normal and Cancerous Fibroblasts . . . .*
Shawgo et al. (Current Opinion in Solid State and Materials Science 6(4), 329-334, 2002) BioMEMS for drug delivery.*
Wolf et al. (Biosensors & Bioelectronics vol. 12. No. 4, pp. 301-309, 1997) Potential of microsensor-based . . . .*
Marquez et al. (Anticanter Reasearch 24: 1347-1352 , 2004) Charge-dependent Targeting . . . .*
G.A.M. Smith, et al, J. Biol. Chem, May 2002, p. 18528-18534, vol. 277, issue 21.
B. Liotta, "CMOS Voltage Comparator Touts 50,000:1 Improvement in Sensor Input Signal Detection", ee Product Center, Oct. 24, 2004.
S.D. Smelt, J. Am. Chem. Soc., p. 14480-14482, vol. 130, 2008.
A.L.Z. Lee, et al, Biomaterials, vol. 30, p. 919-927, 2009.
T. Desai, Nano Lett., vol. 9, p. 716-720, 2009.
European Patent Office, Extended Search Report issued on EP patent application No. 10797693.8, dated Feb. 7, 2014.

* cited by examiner

*Primary Examiner* — Tigabu Kassa
(74) *Attorney, Agent, or Firm* — Weisun Rao; Greenberg Traurig, LLP

(57) ABSTRACT

A drug delivery method for effective drug application is disclosed in this invention. In this method, a micro-carrier delivers an encapsulated, desired drug directly to targeted sites without significant interactions with other components in the biological system in the pathway. In one embodiment, a micro-carrier containing encapsulated drug is first delivered to the general area for treatment. It then scans the area and selectively attaches itself the cell site or organ location to be treated. Finally, the desired drug contained in the micro-carrier is released to the attached cell or organ. In another embodiment, a micro-device is first used to process the general area to be treated to enhance differentiation in properties (such as surface charge) between healthy cells and unhealthy cells (such as cancer cells). Drug encapsulated in the micro-carrier is next applied to preferentially attach onto the targeted sites (such as cancer cell sites) to be treated. Finally, drug is released from the micro-carrier onto the sites to be treated. Such micro-carrier preferably contains multiple functions comprised of at least two functions from the group of sensing, analyzing, logic processing, surface treatment, position detection, motion, injecting, delivering, cutting functions, removing functions, biodegradation and disintegration.

32 Claims, 6 Drawing Sheets

METHOD OF DRUG DELIVERY

CROSS-REFERENCE TO RELATED APPLICATIONS

Not Applicable

FEDERALLY SPONSORED RESEARCH

Not Applicable

BACKGROUND

Conventional drug delivery today most commonly involves either drug injection into a biological body, or tablet or liquid intake from the mouth. Each of these delivery approaches are non-selective, external, uncontrolled and highly prone to interactions with various chemical and biological components within the biological system prior to the drug reaching its target sites. This non-selective approach means that in certain treatments (such as cancer treatment), both healthy cells and unhealthy cells (such as cancer cells) are equally exposed to the same drug at the same dosage. Such external and uncontrolled approaches provide a long pathway from the point at which the drug is introduced into the system and where it is actually applied to its targeted site. Also, the drug dosage cannot be precisely controlled since the drug's concentration may change along the biological pathway from the introduction point to the targeted site due to many factors which include but are not limited to metabolism. In fact, there are no current methodologies which determine, in real time, the degree of drug adsorption or absorption at the targeted site on a microscopic level in a living biological system.

Traditional drug delivery methods have been mainly limited to liquid injection and administration (in tablet or capsule form) in-take through the mouth. In recent years, nano-particles have been proposed and evaluated for drug delivery applications, mostly involving carrying drugs inside or on the surface of such nano-particles. [See S. D. Smedt, J. Am. Chem. Soc. 130, pp. 14480-14482 (2008); A. L. Z. Lee, et al., Biomaterials, 30, pp. 919-927 (2009); T. Desai, Nano Lett. 9, pp. 716-720 (2009); R. O. Esenaliev, U.S. Pat. No. 6,165,440; P. S. Kumar, et al., U.S. Pat. No. 7,182,894; C. J. O'Conner, et al., US Patent Application#20020068187; S. A. Herweck, et al., US Patent Application#20040236278; H. Hirata, et al., US Patent Application#20070243401; G. S. Yi, et al., US Patent Application#2009008146].

For example, A. Chauhan, et al., disclosed a drug delivery system comprising a contact lens in which nano-particles are dispersed with drug encapsulated in the said nano-particles (See US Patent Application #20040096477). Most of the proposed approaches using nano-particles lack the following basic functions and abilities: (a) to reach its targets location in a controlled manner, (b) selectivity and specificity to its intended targets (such as cancer cells), (c) the ability to avoid interactions with the environment on its way to its intended target(s), (d) a controlled release mechanism at a microscopic level (for example, releasing drug only to a specific cell and not to its surrounding area), and (e) bio-degradability of the nano-particle after its use. Very few have contemplated approaches which selectively target treatment sites. J. S. Minor, et. al. (US patent application #20060040390) proposed the use of a biological "key" molecule to recognize targets. A. Manganaro, et al. proposed a method (US patent application #20080279764) in which an ascorbate on the surface of nano-carrier is used to react with the super oxides produced by the cells, with an expected result of enhanced reactions between anti-cancer agent in the carrier and the cancer cells. While the above mentioned prior art attempts to target treatment, the applicability is relatively narrow and lacks the ability to target a wide range of cells/tissues/organs and diseases. Further, the "key" molecule or ascorbate on the surface of nano-carriers mentioned in the Minor and Manganaro applications are likely to react with the environment in the living body and will thus have many difficulties in reaching its intended targets while still in its original form.

In addition to the above stated limitations, the prior art drug delivery approaches also appear to lack general applicability and practicality. The novel drug delivery method disclosed in the current application overcomes the above-mentioned limitations and problems in the prior art. The current, disclosed method has multiple, clearly and strongly differentiated innovations in its integrated drug delivery system which is capable of positioning, sensing (microscopic properties of cells, tissues, and organs), analyzing, logic decision making, drug storage, and drug releasing in a controlled, targeted, and microscopic manner. The disclosed targeted treatment is achieved via measurements of microscopic parameters including but not limited to surface charge, surface voltage, resting potential, absorption and adsorption properties, local pH, Local chemical compositions, local biological compositions and cell compositions. The integrated micro-carrier for drug delivery is fabricated using techniques in microelectronics, with various components including positioning, sensing, analyzing, logic processing, and drug storage and drug release units integrated onto the same chip.

The problems discussed above in today's drug delivery approaches may be responsible for the relatively large discrepancy between laboratory drug tests and clinic drug trials, where many promising drugs in laboratory tests (on animals such as rats) which show clinical efficacy have been proven ineffective in human tests. Further, for diseases such as cancer, nearly all drugs have been ineffective and/or toxic to the human body. To date, there is no technology enabling a direct and selective drug delivery directly to a targeted site within the biological system. It is highly possible that most of the drugs in the existing application techniques have various degree of interaction with various chemical and biological components in a live biological system that negatively affects the drug's efficacy. In the case of treatment utilizing cancer drugs, even if the drug reaches its targeted cancer cells, its strength (concentration) and chemical composition could have been altered, rendering the drug relatively ineffective. Further, there have been no drug delivery methodologies which can be delivered at the cellular level (such as a desired drug injection into a cell through the cell membrane) with controllability and selectivity. Finally, detailed reaction mechanisms as well as absorption/adsorption issues between the drug and its targeted site are not fully understood in a live biological system.

Many cancer treatment drugs have not shown their expected promising results in human trials, even though tests on laboratory animals have shown to be successful. The inventors of this method believe that there are major issues relating to successful and effective drug delivery to the targeted cancer cells. Since such drugs are often taken in tablet/capsule, liquid form (via oral intake) or injection into the biological system, there exist serious issues in reaching the targeted cancer sites in a controlled and effective manner.

For both disease prevention and treatment purposes in modern medicine, there is a critical and urgent need to significantly improve the current drug delivery methodology and approach.

SUMMARY

The invention disclosed is a novel drug delivery method in which a drug encapsulated in a micro-carrier is delivered to its targeted site in a live biological system for improved drug efficacy and to minimize interactions with other components in the biological system. In one embodiment of utilizing this method, it is preferred that a drug is delivered to its targeted site such as a cell, a DNA, bacteria, or an organ with a degree of high selectivity. Specifically, the drug is only applied selectively to the site to be treated (such as directly to a cancer cell during a cancer treatment) and it is not released to the unintended site (such as normal cells during a cancer treatment).

Another unique aspect of the method disclosed herein involves the deployment of a pre-treatment process prior to releasing the drug, to enhance the difference between the targeted site and unintended site. Such pre-treatments thereby increase the degree of drug application selectivity and accuracy to the target area or areas upon which the drug is to be released. This pre-treatment process results in enhancing and/or measuring the difference in properties (such as surface charge, surface potential, surface wetting property, etc.) between the targeted site and unintended site to further enhance the drug selectivity and accuracy.

The preferred drug delivery method relies on multiple operating steps using a micro-carrier with integrated, multiple components, fabricated using technologies such as microelectronics and integrated circuit manufacturing technologies with minimum feature sizes as small as 0.1 micron. Finally, yet another embodiment of this invention utilizes selective absorption or adsorption of said micro-carrier onto healthy or unhealthy cells (such as cancer cells) to achieve selective drug release only into or onto the targeted cells (such as cancer cells during cancer treatment).

BRIEF DESCRIPTION OF THE DRAWINGS

These and other features, aspects and advantages of the present invention will become better understood with regard to the following description, appended claims and accompanying drawings where:

DESCRIPTION

A novel drug delivery method is disclosed in this application in which a drug encapsulated in a micro-carrier is delivered to its targeted site in a live biological system for improved efficiency and to minimize interactions with other components in the biological system. In one embodiment of utilizing this method, it is preferred that a drug is delivered to its targeted site such as a cell, a DNA, bacteria, and an organ with a degree of high selectivity. Specifically, it is only applied selectively to the site to be treated (such as cancer cells during a cancer treatment) and it is not released to the un-intended site (such as normal cells during a cancer treatment).

Figure 1:
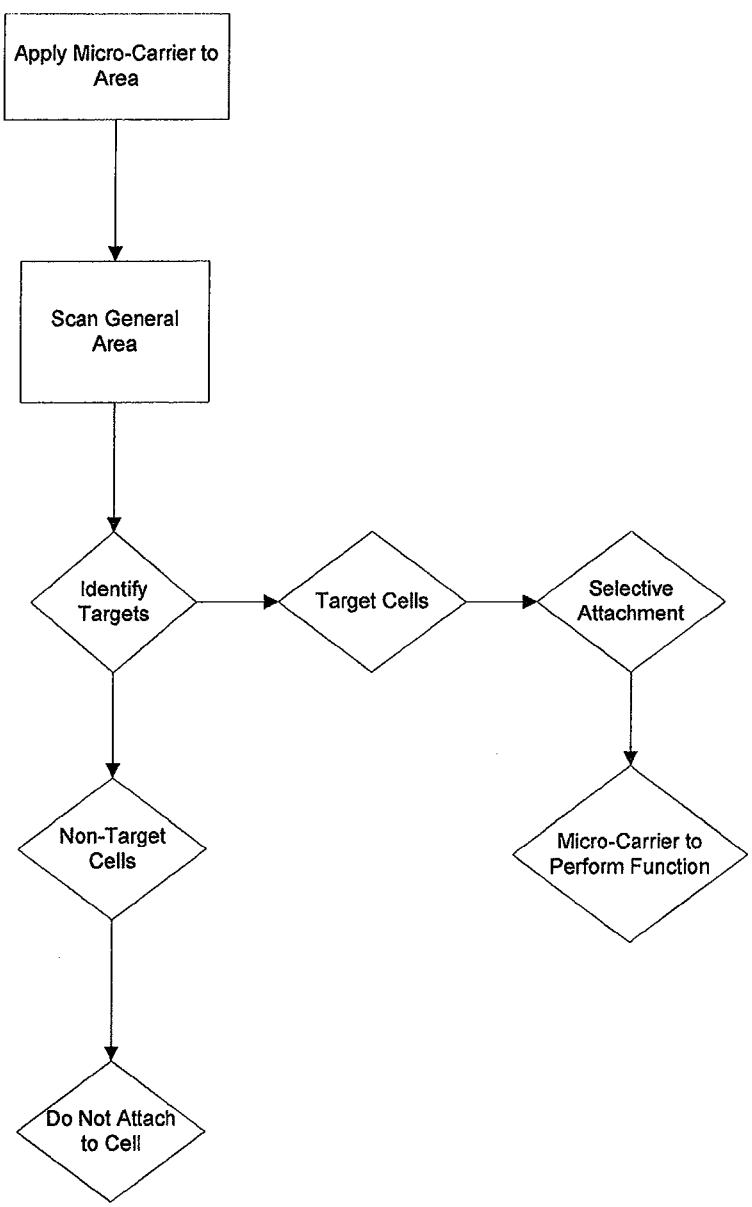
FIG. 1 illustrates a preferred method of delivering drug to target cells utilizing micro-devices.

One preferred delivery process flow is shown in FIG. 1. whereby a micro-carrier is applied to an area, the micro-carrier scans the general area and identifies targets. If the cell is a target cell, the micro-carrier selectively attaches to the cell and performs a function at the cellular level. If the cell is a non-targeted cell, the micro-carrier does not attach to the cell. This method allows for selective attachment at the cellular level so that the desired function only affects the targeted cells.

In this invention, optionally, a micro-carrier can integrate, in addition to other components, a micro-motor and a position detection unit to travel to its intended target location. Optionally, said micro-carrier is integrated with multiple components with multiple functions including but not limiting to positioning, sensing, data collection, data analysis, decision making, selective drug release onto targeted cells or tissues or organs, and disintegration.

Figure 2:
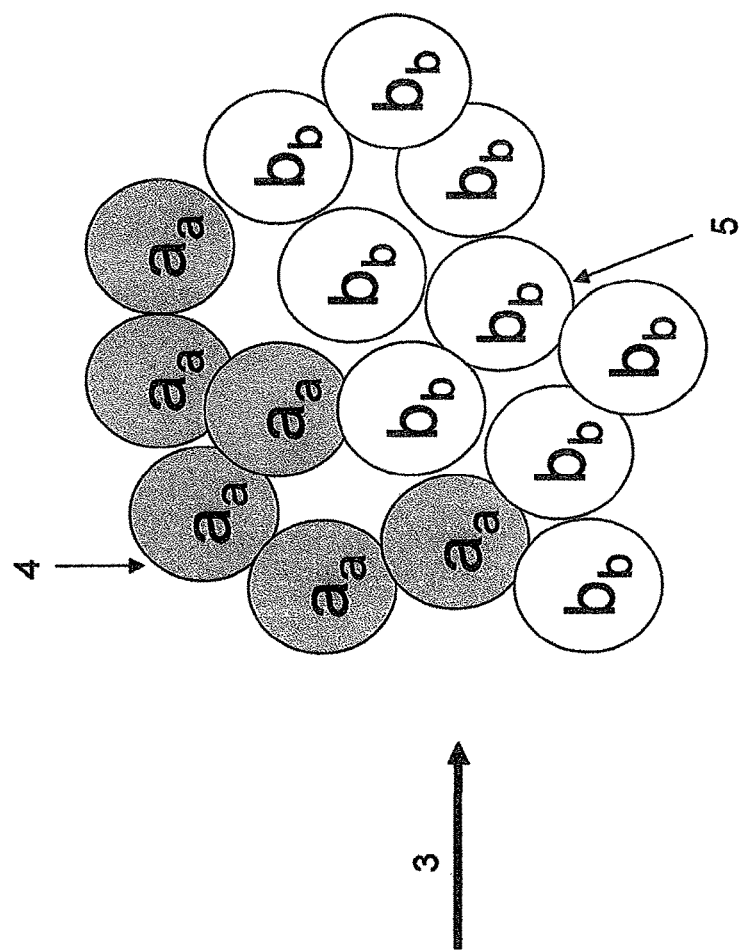
FIG. 2 illustrates a method of applying a pre-treatment to two different types of cells causing each type of cell to manifest a specific charge.
Figure 2:
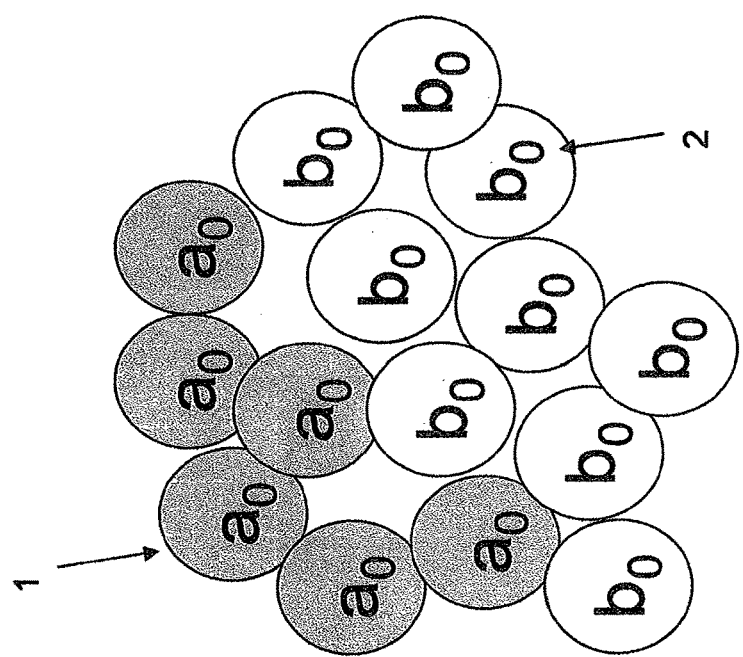

In another embodiment, prior to drug release, a pre-treatment process 3 shown in FIG. 2 is utilized to enhance the difference between the cells at the targeted site and cells at the unintended site. This method increases the degree of drug application selectivity and accuracy to the target upon which the drug is to be released. FIG. 2 shows a group of "a" cells 1 each having a charge of "$a_0$" (which could be zero) and a group of "b" cells 2 also having a charge of "$b_0$" (which could also be zero). Upon pre-treatment 3, the "a" cells 4 now have charge "$a_a$" and the "b" cells 5 now have charge "$b_b$," allowing for differentiation between the two differently charged groups of cells. After pre-treatment, the difference in surface charge, $a_a-b_b$, between cell "a" and cell "b", is enhanced, making it increased over the difference in charge between cell "a" and cell "b" prior to the pre-treatment, $a_0-b_0$, making identification of cell types much easier and resulting in much more efficient and accurate targeted treatment. In addition to surface charge, this pre-treatment process can also be used to enhance the difference between the targeted site and unintended site in at least one of the properties comprised of surface charge, surface resting potential, conductivity, surface current, bulk current, surface adsorption properties, surface absorption properties, surface tension, optical properties, pH, chemical compositions, biological properties, biological composition, density, friction and acoustical properties.

Figure 3:
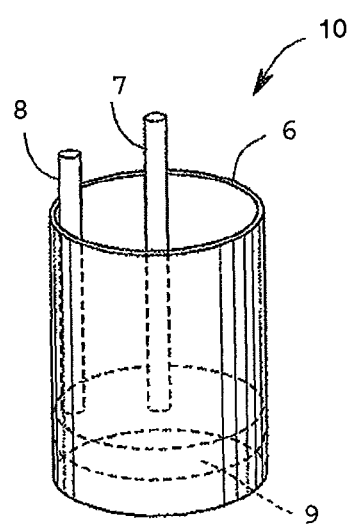
FIG. 3 illustrates a perspective view of a micro-carriers with a sensing unit, logic unit and micro-injector.
Figure 4:
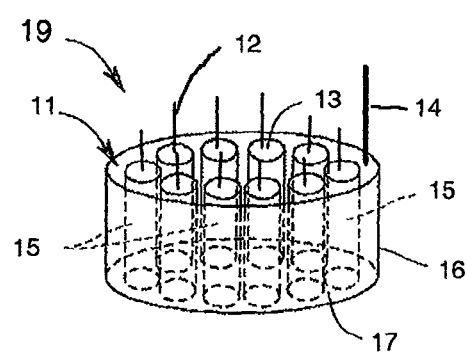
FIG. 4 illustrates a perspective view of a micro-carriers with multiple columns of injectors.

As disclosed herein, the drug delivery process is accomplished through the use of a micro-carrier, which has a size ranging from about 2 angstroms to about 5 millimeters, with a preferred embodiment size range from 100 angstroms to 500 microns. In one embodiment, the said micro-carrier is made up of a sensor, a micro-container containing the desired drug to be delivered, and a micro-injector. A disclosed micro-carrier 10 with a sensing unit 8, a logic unit 9 and a micro-injector 7 is shown in FIG. 3. As shown in FIG. 4, a micro-carrier 19 with multiple drug columns 15 which enhance drug delivery efficiency, a sensor 14, multiple micro-injectors 12, an outer membrane 16, an underside 17 and a top side 11.

The preferred drug delivery method relies on multiple operating steps using a micro-carrier with integrated, multiple components including but not limited to a micro-sensor, a micro-container, a micro-needle, a micro-injector and, optionally, a logic processing unit, a memory unit, a signal transmitter, a receiver, a position detection unit and a micro-motor for carrying out multiple operating steps, utilizing their wide range of novel functions achieved through functionality integration at the microscopic level and the state-of-the-art micro-device fabrication techniques such as those found in integrated circuit fabrication techniques currently used in the microelectronics field.

In one embodiment, a micro-carrier with at least one drug-containing compartment, one sensor, one logic processing unit, and one drug injector attached to the drug compartment integrated in the carrier is applied to a general area in a living body where a drug is to be released to its targeted cells, tissues, or organs. First, the said sensor scans the general area and collects at least one of the local parameters at the cellular, tissue or organ level, selected from the group of surface charge, surface resting potential, conductivity, surface current, bulk current, surface adsorption properties, surface adsorption properties, surface tension, optical properties, chemical compositions, biological properties, biological composition, density, friction, local pH, local chemical properties, local chemical emission and presence, local biological species and presence and acoustical properties. Next, the collected information and data is processed through the logic processing unit to determine the intended target for drug release (for example, a cancer cell). Once the targeted cell, tissue or organ is determined, the injector of said micro-carrier is moved to the surface of the target and injects the drug into the target. As a specific example, in this novel patent application, upon arrival at its general treatment location, a voltage comparator integrated onto a micro-carrier is first used to measure resting potential on a cell surface, thereby determining whether the measured cell is likely a cancer cell. In the state-of-the-art voltage comparator technology, a voltage as low as sub-1 mV can be measured (See "CMOS Voltage Comparator Touts 50,000:1 Improvement in Sensor Input Signal Detection", Bettyann Liotta, ee Product Center (Oct. 25, 2004)), while resting potential at the cellular level in a human body is typically on the order of 10 mV. Further, it has been reported that polarization of cells seems to reflect on the state of cells, including the state of cell mitosis, with normal cells being very hyperpolarized and cancerous cells being very depolarized. The membrane potential appears to be correlated to the state of mitosis of cells (See G. A. M. Smith, et al., J. Biol. Chem., Vol. 277, Issue 21, 18528-18534, (May 2002)). Therefore, an advanced voltage comparator can be integrated onto the micro-carrier disclosed in this patent application which is capable of measuring resting potential at cellular levels, as well as identifying and differentiating cancerous cells from normal cells, with normal cells having a higher resting potential.

Yet another embodiment of this invention is the use of selective absorption or adsorption of a micro-carrier onto healthy (such as normal cells) or unhealthy cells (such as cancer cells) to achieve selective drug release only onto the targeted cells (cancer cells in cancer treatment).

The word "absorption" typically means a physical bonding between the surface and the material attached to it (absorbed onto it, in this case). On the other hand, the word "adsorption" generally means a stronger, chemical bonding between the two. Those properties are very important in this invention, because they can be effectively used for targeted drug treatment.

In terms of selective adsorption and absorption of the said micro-carrier onto targeted surface, first, a micro-carrier is applied to the general area where drug is to be released to its target (optionally, the micro-carrier can travel to the intended general area on its own through the use of a micro-motor, position detector, logic unit, and sensor). Next, optionally, a pre-treatment step can be carried out by releasing a designed solution from the micro-carrier to treat the general area, thereby enhancing the difference in surface properties of normal cells and diseased cells. In general, normal cells have different surface properties than those of diseased cells. For example, normal cells typically have higher resting potential (membrane potential) than that of cancerous cells. Therefore, upon supplying negative charge on cell surfaces in a designed pre-treatment, the relatively low resting potential on a cancer cell could be relatively easily switched to zero and even negative potential while normal cells can still maintain at a positive potential. In this way, a micro-carrier with a positive surface charge (which can be controlled with a designed micro-carrier) can be selectively attached to cancerous cells and not on the normal cells (since alike charges repel each other). As another example, since normal and diseased cells likely have different surface chemistries, a micro-carrier can have a designed surface chemistry to be preferentially adsorbed onto diseased cells.

The method of utilizing micro-carriers disclosed in this patent application has a wide range of designs, structures and functionalities. It involves the integration of multiple components onto a micro-carrier using including but not limiting to microelectronics techniques used in integrated circuit fabrication, with a minimum feature size of as small as 0.1 micron. Its core components are micro-sensors, micro-containers (for storage drug(s)), micro-injectors, micro-processing units, memory units and micro-needles. Additionally, it may also include but is not limited to a voltage comparator, four-point probe, calculator, position detection unit, micro-motor, logic circuitry, memory unit, micro-cutter, micro-hammer, micro-shield, micro-dye, micro-pin, micro-knife, micro-thread holder, micro-tweezers, micro-optical absorber, micro-mirror, micro-shield, micro-wheeler, micro-filter, micro-chopper, micro-shredder, micro-pumps, micro-absorber, micro-signal detector, micro-driller, micro-sucker, signal transmitter, signal generator, friction sensor, electrical charge sensor, temperature sensor, hardness detector, acoustic wave generator, optical wave generator, heat generator, micro-refrigerator and charge generator.

It should be noted that advancements in manufacturing technologies have now made fabrications of a wide range of micro-devices such as micro-carrier disclosed in this application and integration of various functions onto the same device highly feasible and cost effective. For example, a typical human cell size is about 10 microns. Using the state-of-the-art integrated circuit fabrication techniques, the minimum feature size which can be defined on a micro-device can be as small as 0.1 micron. One good example is the design and fabrication of micro-electro-mechanical devices (MEMS), which now are being used in wide of applications. In terms of materials for micro-devices, the general principle is a materials compatibility with the biological materials that it will come in contact.

Figure 5:
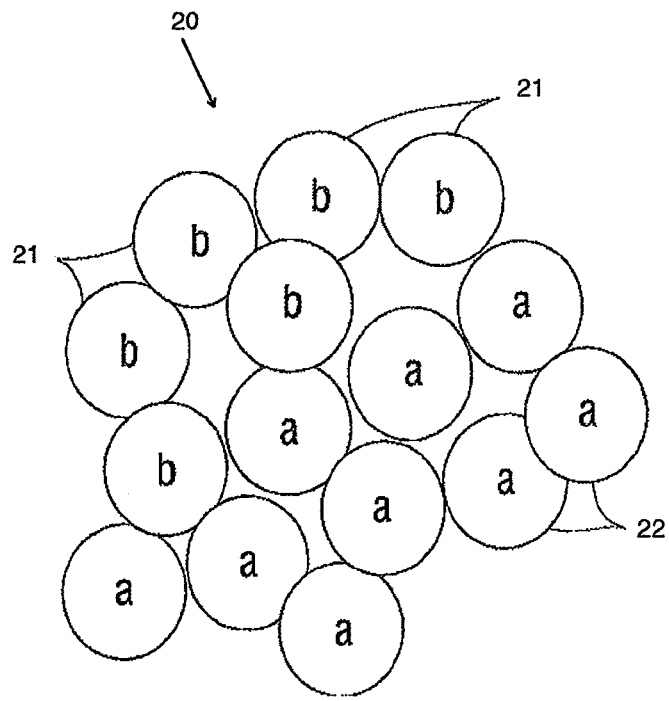
FIG. 5 illustrates a perspective close up view of a group of healthy cells and a group of unhealthy, cancerous cells.
Figure 6:
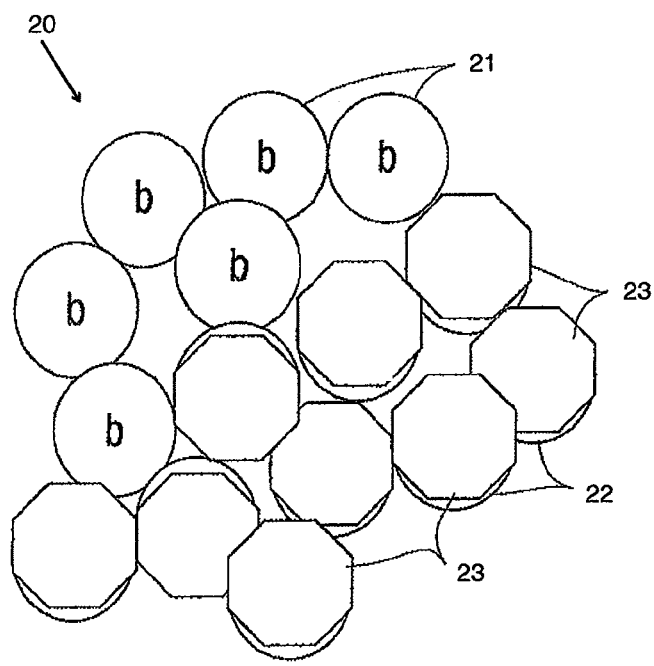
FIG. 6 illustrates a perspective close up view of a group of healthy cells and a group of unhealthy cells (cancerous cells for example) with micro-carriers either adsorbed or absorbed onto the unhealthy cells only.

Next, several examples will be used to illustrate embodiments of this invention. As shown in FIG. 5 and FIG. 6, in a preferred drug delivery process, micro-device 23 comprising a sensing unit, a micro-container with desired drug(s), a micro-injector and optionally, a logic processing unit, a memory unit, a signal transmitter and a receiver are utilized. Such micro-device is designed in a way that it will preferentially absorb (or adsorb) only onto cancer cells "a" 22 and not to healthy cells "b" 21. Once the micro-device 23 is attached to the cancer cell "a" 22, it will inject cancer-killing agent(s) into the cancer cell "a" 22. To make sure that no healthy cells "b" 21 are killed due to error in attachment, a logic unit may be used to make a correct decision based on the sensed data on the attached cell. Since this novel approach is a targeted approach with cancer-killing drug directly delivered to the cancer cells, it is expected that it effectiveness can be greatly improved, while leaving healthy cells unharmed.

This novel approach is ideally suited for targeted medical treatment to destroy unhealthy cells or organ portion while minimizing damage to the healthy cells or organ parts. In contrast to existing drug delivery approaches, this inventive process has a high degree of selectivity and efficiency, and it is microscopic, non-intrusive and well controlled.

Figure 7:
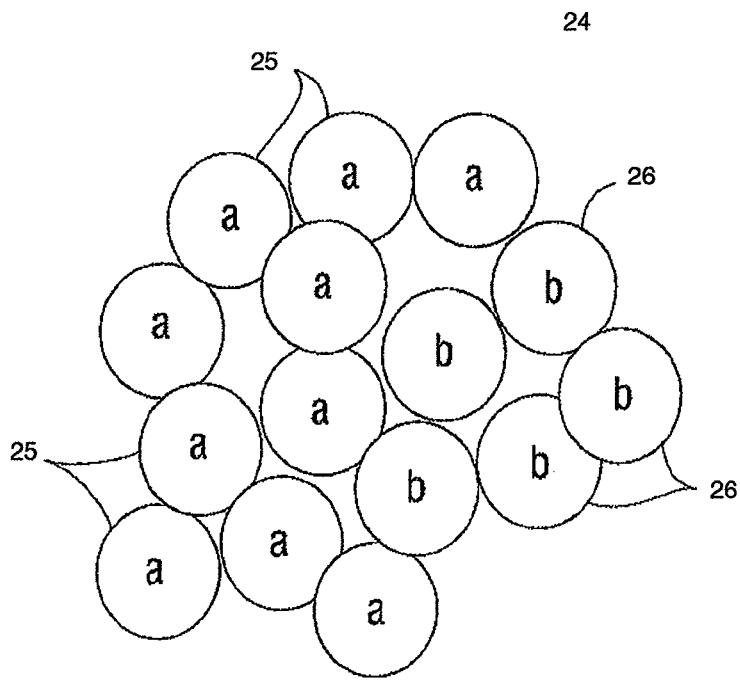
FIG. 7 illustrates a perspective close up view of a group of healthy cells and a group of unhealthy, cancerous cells.
Figure 8:
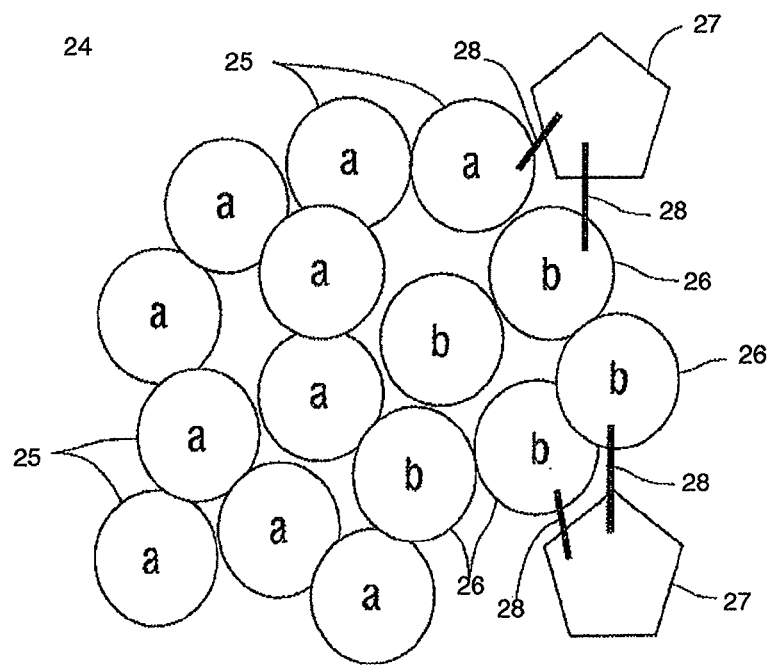
FIG. 8 illustrates a perspective close up view of a group of healthy cells and a group of unhealthy, cancerous cells with micro-carriers acting as a voltage comparator on both sets of cells.

Since it is critical to identify healthy cells from the unhealthy cells (such as cancer cells) for targeted drug delivery, a micro-carrier containing a micro-sensor can be utilized to detect a cancer cell in a living organ in a non-intrusive manner. The micro-sensor with a voltage comparator in the said micro-carrier is first calibrated by measuring surface charge (or voltage) at known healthy cells. Next, as shown in FIG. 7, an area of cells 24 containing healthy cells "a" 25 and unhealthy cells "b" 26. In FIG. 8, to the same area of cells 24, healthy cells "a" 25 and unhealthy cells "b" 26 voltage comparators 27 attach via probes 28 to both healthy and unhealthy cells and scan the area. By comparing voltages at cell surface (or charge), unhealthy cells such as cancer cells can readily be differentiated from the healthy cells. The micro-carrier is next instructed to attach itself to the identified, targeted site (for example, a cancer cell site). Upon attachment, a drug can be directly delivered into the targeted site using a micro-injector in the micro-carrier. It should be pointed out that a micro-carrier can be integrated with a voltage comparator, a logic circuitry unit, a micro-container, and a micro-injector (or micro-needle).

The reader's attention is directed to all papers and documents which are filed concurrently with this specification and which are open to public inspection with this specification, and the contents of all such papers and documents are incorporated herein by reference. All the features disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example of a generic series of equivalent or similar features.

Any element in a claim that does not explicitly state "means for" performing a specific function, or "step for" performing a specific function, is not to be interpreted as a "means" or "step" clause as specified in 35 U.S.C. § 112 para. 6. In particular, the use of "step of" in the claims herein is not intended to invoke the provisions of 35 U.S.C. § 112 para. 6.

What is claimed is:

1. A micro-carrier for delivering a first drug to a live biological system, comprising:
   (a) a first micro-container within the micro-carrier to encapsulate the first drug;
   (b) a sensor that is integrated to the micro-carrier, wherein the sensor scans a general area in the live biological system, detects a property of the general area and identifies a targeted site for selectively attaching the micro-carrier to the targeted site by comparing the measured property of the targeted site and the non-targeted site; or a surface material that absorbs or adsorbs the micro-carrier to a targeted site; and
   (c) an injector attached to the first micro-container for delivering the drug from the first micro-container to the targeted site,
   wherein the sensor is a voltage comparator that measures the resting potential on a cell surface and identifies cancerous cells from normal cells;
   wherein the micro-carrier further comprises a pre-treatment unit, configured for releasing a designed solution from the micro-carrier to treat the general area, thereby enhancing the difference in surface properties of the normal cells and the cancerous cells before the drug is released;
   wherein micro-container is made of a bio-compatible inorganic material, a bio-compatible semiconductor material, or a biodegradable material;
   wherein the micro-carrier has a size ranging from 100 angstroms to 500 microns.

2. The micro-carrier of claim 1, further comprising an additional micro-container within the micro-carrier to encapsulate a drug different from the first drug.

3. The micro-carrier of claim 2, wherein the micro-carrier releases the different drugs sequentially at a controlled rate and at a desired time interval between the different drugs.

4. The micro-carrier of claim 1, wherein the targeted site comprises cancerous cells and the non-targeted site is free of cancerous cells.

5. The micro-carrier of claim 1, wherein the property is surface charge, surface resting potential, conductivity, surface current, bulk current, surface adsorption property, surface adsorption property, surface tension, optical property, chemical compositions, biological property, biological composition, density, friction, local pH, local chemical property, local chemical emission and presence, local biological species and presence, or acoustical property.

6. The micro-carrier of claim 1, wherein the targeted site comprises cells, a DNA structure, tissue, bacteria, or an organ.

7. The micro-carrier of claim 1, wherein the first drug is a cell membrane receptor protein, an epidermal growth factor receptor, an insulin-like growth factor type 1 receptor, or a vascular endothelial growth factor receptor.

8. The micro-carrier of claim 1, further comprising a position detector, a logic processing unit, a memory unit, a micro-motor, a signal transmitter, a signal receiver, a micro-needle, a micro-knife, micro-tweezers, a micro-cutter, a micro-hammer, a micro-shield, a micro-dye, a micro-pin, a micro-knife, a micro-thread holder, a micro-optical absorber, a micro-mirror, a micro-shield, a micro-wheeler, a micro-filter, a micro-chopper, a micro-shredder, a micro-pump, a micro-absorber, a micro-signal detector, a micro-driller, a micro-sucker, a signal generator, a friction sensor, an electrical charge sensor, a temperature sensor, a hardness detector, an acoustic wave generator, an optical wave generator, a heat generator, a micro-refrigerator, or a charge generator.

9. The micro-carrier of claim 8, wherein the logic processing units capable of analyzing the data collected by the sensor or the position detector before the drug is released and optionally making a decision for the a next move.

10. The micro-carrier of claim 8, wherein the micro-motor is capable of moving the micro-carrier to the general area or the targeted site, optionally by following the instruction of the logic processing unit or the position detector.

11. The micro-carrier of claim 1, wherein the biodegradable material is a natural biological material, a synthesized biological material, a synthesized polymer material, or an organic material.

12. The micro-carrier of claim 11, wherein the biodegradable, synthesized polymer material has a backbone comprising an amide, anhydride, or ester group.

13. The micro-carrier of claim 1, wherein the micro-carrier is capable of disintegrating into pieces smaller than one micron after its use.

14. The micro-carrier of claim 1, wherein the micro-carrier is fabricated by an integrated circuit production process comprising microelectronics manufacturing technologies.

15. The micro-carrier of claim 1, wherein the micro-carrier is for the treatment of cancer, diabetes, or blood related diseases.

16. A method for delivering a first drug to a live biological system comprising a step of introducing a micro-carrier of claim 1 into the live biological system.

17. The method of claim 16, further comprising the following steps: (a) applying the micro-carrier containing the desired drug to a general area within the biological system to be treated and (b) releasing the drug from the micro-carrier to the general area within the biological system to be treated.

18. The method of claim 16, further comprising the following steps: (a) applying the micro-carrier containing the desired drug to a general area to be treated; (b) scanning the general area to be treated; (c) identifying the targeted site to be treated; (d) selectively attaching the micro-carrier to the targeted site, and (e) releasing the drug to the targeted site to be treated.

19. The method of claim 16, further comprising the following steps: (a) applying the micro-carrier to a general area to be treated; (b) treating the general area by the micro-carrier to enhance the difference in a property of a targeted site and of a non-targeted site; (c) scanning the general area to be treated; (d) identifying the targeted site to be treated; (e) selectively attaching the micro-carrier to the targeted site to be treated, and (f) releasing the drug from the micro-carrier to the targeted site to be treated.

20. The method of claim 16, further comprising the following steps: (a) applying the micro-carrier to a general area to be treated; (b) treating the general area by the micro-carrier to enhance the difference in a property of a targeted site and of a non-targeted site; (c) applying the micro-carrier containing at least one desired drug to the general area to be treated; (d) scanning the general area to be treated; (e) identifying the targeted site to be treated; (f) selectively attaching the micro-carrier to the targeted site to be treated; and (g) releasing the drug from the micro-carrier to the targeted site to be treated.

21. The method of claim 16, further comprising the following steps: (a) making the micro-carrier travel to a general area to be treated by a micro-motor, a position detection unit, or a logic unit integrated to the micro-carrier; (b) scanning the general area to be treated by a sensor in the micro-carrier and collecting the data of physical, chemical, biological, mechanical, optical, or acoustical parameters in the general area; (c) analyzing the collected set of data; (d) identifying a targeted site to be treated; e) selectively attaching the micro-carrier to the targeted site to be treated; (f) releasing the drug from the micro-carrier to the targeted site to be treated and (g) optionally, distintegrating the micro-carrier into small pieces of individual size smaller than one micron.

22. The method of claim 16, further comprising the following steps: (a) applying the micro-carrier to a general area to be treated; (b) optionally, treating the general area by the micro-carrier to enhance the difference in a property of a targeted site and of a non-targeted site; (c) sensing the general area and collecting data by a sensor; (d) analyzing the data collected by the sensor; e) making a next move by the micro-carrier; and (f) optionally, disintegrating the micro-carrier into small pieces of individual size smaller than one micron.

23. The method of claim 16, further comprising the following steps: (a) applying the micro-carrier to a general area or making the micro-carrier travel to a general area by a micro-motor, a position detector, a logic unit, or a sensor; (b) optionally, treating the general area by the micro-carrier to enhance a difference in a property of a targeted site and of a non-targeted site; (c) selectively absorbing or adsorbing the micro-carrier to the targeted site; (d) releasing the drug to the targeted site; and (e) optionally, disintegrating the micro-carrier into small pieces of individual size smaller than one micron.

24. The method of claim 16, further comprising a step of using a voltage comparator integrated to the micro-carrier to measure resting potential on a cell surface and identify a targeted site to be treated.

25. The method of claim 19, wherein the property, in which the difference is enhanced by the micro-carrier, is surface charge, surface resting potential, conductivity, surface current, bulk current, surface adsorption property, surface adsorption property, surface tension, optical property, chemical compositions, biological property, biological composition, density, friction, or acoustical property.

26. The method of claim 16, wherein the targeted site comprises cells, a DNA structure, bacteria, or an organ.

27. The method claim 16, wherein the method is for cancer treatment.

28. The method of claim 16, further comprising a step of releasing one or more drugs at a controlled rate and at a desired time interval between the different drugs for maximizing the effects of the released drugs.

29. The method of claim 16, further comprising a step of disintegrating the micro-carrier into small pieces of individual size smaller than one micron.

30. The method of claim 16, further comprising a step of moving the micro-carrier to the targeted site by using a micro-motor integrated on the micro-carrier.

31. The method of claim 16, further comprising a step of moving the micro-carrier to the targeted site by using a micro-motor, a position detection device, or a logical processing unit integrated to the micro-carrier; wherein the position detection device or the logic processing unit provides instructions to the micro-motor for its next movement.

32. The method of claim 16, further comprising a step of moving the micro-carrier to the targeted site by using a micro-motor, a position detection device, a sensor, or a logic processing unit integrated to the micro-carrier; wherein the position detection device, the sensor, or the logic processing provides instructions to the micro-motor for its next movement, based on information on (a) a carrier position detected by the position detection device, or (b) a local environment signal sensed by the sensor.

* * * * *